(12) United States Patent
Lord

(10) Patent No.: US 9,211,204 B2
(45) Date of Patent: Dec. 15, 2015

(54) POLYMERIC STENTS AND METHOD OF MANUFACTURING SAME

(71) Applicant: Abbott Cardiovascular Systems Inc., Santa Clara, CA (US)

(72) Inventor: Brenna Hearn Lord, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 127 days.

(21) Appl. No.: 13/951,139

(22) Filed: Jul. 25, 2013

(65) Prior Publication Data

US 2013/0310921 A1    Nov. 21, 2013

Related U.S. Application Data

(60) Continuation of application No. 13/758,741, filed on Feb. 4, 2013, now Pat. No. 8,495,904, which is a division of application No. 12/772,155, filed on Apr. 30, 2010, now Pat. No. 8,370,120.

(51) Int. Cl.

| | | |
|---|---|---|
| *G06G 7/48* | (2006.01) | |
| *A61F 2/89* | (2013.01) | |
| *A61F 2/82* | (2013.01) | |
| *B23K 26/38* | (2014.01) | |
| *B23K 26/40* | (2014.01) | |

(52) U.S. Cl.
CPC ... *A61F 2/89* (2013.01); *A61F 2/82* (2013.01); *B23K 26/38* (2013.01); *B23K 26/4065* (2013.01); *A61F 2240/00* (2013.01); *B23K 2201/06* (2013.01); *B23K 2203/00* (2013.01); *Y10T 29/49826* (2015.01)

(58) Field of Classification Search
CPC ............ A61F 2/07; A61F 2/82; C08G 63/02; C08G 63/08; C08L 67/04
USPC ................. 703/6, 11; 623/1.15, 1.16; 264/51, 264/209.1, 532, 563; 83/54; 525/41; 522/111

See application file for complete search history.

(56) References Cited

U.S. PATENT DOCUMENTS

| | | | |
|---|---|---|---|
| 2010/0004735 A1* | 1/2010 | Yang et al. | 623/1.16 |
| 2010/0094405 A1* | 4/2010 | Cottone | 623/1.16 |
| 2010/0252965 A1* | 10/2010 | Wang et al. | 264/563 |
| 2010/0256740 A1* | 10/2010 | Limon et al. | 623/1.16 |
| 2011/0021717 A1* | 1/2011 | Wang et al. | 525/411 |
| 2011/0049751 A1* | 3/2011 | Gada et al. | 264/209.1 |
| 2011/0056350 A1* | 3/2011 | Gale et al. | 83/54 |

(Continued)

*Primary Examiner* — Kandasamy Thangavelu
(74) *Attorney, Agent, or Firm* — Squire Patton Boggs (US) LLP

(57) ABSTRACT

A pattern is used to form a stent scaffold from a polymeric precursor tube having a particular outer diameter. A new pattern can be derived from a base pattern, wherein the new pattern can be used to form a stent scaffold from a precursor tube having an outer diameter $OD_{PR}$ smaller than that needed for the base pattern. The new pattern can be derived by determining the shape of a stent scaffold, having the base pattern, after having been radially compressed to $OD_{PR}$. The radially compressed shape is used to design the new pattern, which is applied to a precursor tube having an outer diameter $OD_{PR}$. The new pattern can have a plurality of W-shaped closed cells, each W-shape closed cell bounded by struts oriented in such a way to form interior angles from about 80 degrees to about 95 degrees between every two adjacent struts.

16 Claims, 10 Drawing Sheets

(56) References Cited

U.S. PATENT DOCUMENTS

2011/0062638 A1* 3/2011 Glauser et al. ................ 264/532
2011/0065825 A1* 3/2011 Lambert et al. ............... 522/111
2011/0066222 A1* 3/2011 Wang et al. .................. 623/1.15
2011/0260352 A1* 10/2011 Tang et al. ...................... 264/51

* cited by examiner

STENT SCAFFOLDS BEFORE CRIMPING AND DEPLOYMENT

New Pattern
applied to $OD_{PR}$=2.5 mm

New Pattern of FIG. 9
applied to $OD_{PR}$=3.0 mm

Base Pattern of FIG. 5
applied to $OD_P$=3.5 mm

STENT SCAFFOLDS AFTER DEPLOYMENT TO
$ID_{DEPLOY}$=3.5 mm; $OD_{DEPLOY}$ approx. 3.8 mm New Pattern
applied to $OD_{PR}$=2.5 mm New Pattern of FIG. 9
applied to $OD_{PR}$=3.0 mm Base Pattern of FIG. 5
applied to $OD_P$=3.5 mm

POLYMERIC STENTS AND METHOD OF MANUFACTURING SAME

CROSS-REFERENCE TO RELATED APPLICATIONS

This application is a continuation of application Ser. No. 13/758,741, filed Feb. 4, 2013, now U.S. Pat. No. 8,495,904, which is a divisional of application Ser. No. 12/772,155, filed Apr. 30, 2010, now U.S. Pat. No. 8,370,120, both of which are incorporated herein by reference in its entirety for all purposes.

FIELD OF THE INVENTION

This invention relates to expandable endoprostheses, and more particularly to methods of manufacturing polymeric stents.

BACKGROUND OF THE INVENTION

An "endoprosthesis" corresponds to an artificial device that is placed inside the body, more particularly, within an anatomical lumen. A "lumen" refers to a cavity of a tubular organ such as a blood vessel. A stent is an example of an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels.

The treatment of a diseased site or lesion with a stent involves both delivery and deployment of the stent. "Delivery" refers to introducing and transporting the stent through an anatomical lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen.

In the case of a balloon expandable stent, the stent is mounted about a balloon disposed on the catheter. Mounting the stent typically involves radially compressing or crimping the stent onto the balloon. The stent is then expanded by inflating the balloon. The balloon may then be deflated and the catheter withdrawn.

The stent must be able to satisfy a number of mechanical requirements. First, the stent must be capable of withstanding the structural loads, namely radial compressive forces, imposed on the stent as it supports the walls of an anatomical lumen. Therefore, a stent must possess adequate radial strength. Radial strength, which is the ability of a stent to resist radial compressive forces, is due to strength and rigidity around a circumferential direction of the stent. Radial strength and rigidity, therefore, may also be described as hoop strength and rigidity.

Once expanded, the stent must adequately maintain its size and shape throughout its service life despite the various forces that may come to bear on it, including the cyclic loading induced by the beating heart. For example, a radially directed force after deployment may cause a stent to plastically deform, which can reduce clinical effectiveness.

In addition, the stent must possess sufficient flexibility to allow for crimping, deployment, and cyclic loading after deployment. Longitudinal flexibility is important to allow the stent to be maneuvered through a tortuous anatomical path and to enable it to conform to a deployment site that may not be linear or may be subject to flexure. Also, the stent must be biocompatible so as not to trigger any adverse responses.

The structure of a stent typically comprises scaffolding that includes a pattern or network of interconnecting structural elements often referred to in the art as struts, links and rings. The scaffolding is designed so that the stent can be radially compressed (to allow crimping) and radially expanded (to allow deployment).

Polymers have been used to make stent scaffolding. The art recognizes a variety of factors that affect a polymeric stent's ability to retain its structural integrity when subjected to external loadings, such as crimping and balloon expansion forces. These interactions are complex and the mechanisms of action not fully understood. According to the art, characteristics differentiating a polymeric, bio-absorbable stent scaffolding of the type expanded to a deployed state by plastic deformation from a similarly functioning metal stent are many and significant. Indeed, several of the accepted analytic or empirical methods/models used to predict the behavior of metallic stents tend to be unreliable, if not inappropriate, as methods/models for reliably and consistently predicting the highly non-linear behavior of a polymeric load-bearing, or scaffolding portion of a balloon-expandable stent. The models are not generally capable of providing an acceptable degree of certainty required for purposes of implanting the stent within a body, or predicting/anticipating the empirical data.

Polymer material considered for use as a polymeric stent scaffolding, such as PLLA and PLGA, may be described through comparison with a metallic material conventionally used to form stent scaffolding. In comparison to metals, a suitable polymer has a low strength to weight ratio, which means more material is needed to provide an equivalent mechanical property to that of a metal. Therefore, struts in polymeric scaffolding must be made thicker and wider to have the strength needed. Polymeric scaffolding also tends to be brittle or have limited fracture toughness. The anisotropic and rate-dependant inelastic properties (i.e., strength/stiffness of the material varies depending upon the rate at which the material is deformed) that are inherent in the material only compound this complexity in working with a polymer, particularly, a bio-absorbable polymer such as PLLA and PLGA.

Therefore, processing steps performed on and design changes made to a metal stent that have not typically raised concerns for unanticipated changes in the average mechanical properties, may not also apply to a polymer stent due to the non-linear and sometimes unpredictable nature of the mechanical properties of the polymer under a similar loading condition. It is sometimes the case that one needs to undertake extensive validation before it even becomes possible to predict more generally whether a particular condition is due to one factor or another—e.g., was a defect the result of one or more steps of a fabrication process, or one or more steps in a process that takes place after stent fabrication, e.g., crimping. As a consequence, a change to a fabrication process, post-fabrication process or even relatively minor changes to a stent pattern design must, generally speaking, be investigated more thoroughly than if a metallic material were used instead of the polymer. It follows, therefore, that when choosing among different polymeric stent designs for improvement thereof, there are far less inferences, theories, or systematic methods of discovery available, as a tool for steering one clear of unproductive paths, and towards more productive paths for improvement, than when making design changes in a metal stent.

It is recognized, therefore, that, whereas inferences previously accepted in the art for stent validation or feasibility when an isotropic and ductile metallic material was used, such inferences would be inappropriate for a polymeric stent. A change in a polymeric stent pattern may affect, not only the stiffness or lumen coverage of the stent in its deployed state, but also the propensity for fractures to develop when the stent is crimped or being deployed. This means that, in comparison to a metallic stent, there is generally no assumption that can be made as to whether a changed stent pattern may not produce an adverse outcome, or require a significant change in a processing step (e.g., tube forming, laser cutting, crimping, etc.). Simply put, the highly favorable, inherent properties of a metal (generally invariant stress/strain properties with respect to the rate of deformation or the direction of loading, and the material's ductile nature), which simplify the stent fabrication process, allow for inferences to be more easily drawn between a changed stent pattern and/or a processing step and the ability for the metallic stent to be reliably manufactured with the new pattern and without defects when implanted within a living being.

A change in the pattern of the struts and rings of a polymeric stent scaffolding that is plastically deformed, both when crimped to, and when later deployed by a balloon, unfortunately, is not as easy to predict as a metal stent. Indeed, it is recognized that unexpected problems may arise in polymer stent fabrication steps as a result of a changed pattern that would not have necessitated any changes if the pattern was instead formed from a metal tube. In contrast to changes in a metallic stent pattern, a change in polymer stent pattern may necessitate other modifications in fabrication steps or post-fabrication processing, such as crimping and sterilization.

A problem encountered with polymeric stents after they are crimped onto a balloon is the development of fractures and other defects that require the stent to be rejected and scrapped. Cracks and other defects can render the stent incapable of functioning properly when fully deployed by the balloon. Another problem is that deployment of polymeric stents from the crimped state to a deployed state in a patient can produce strain that adversely affects the ability of the stent to stay in the deployed state and remain at the implantation site, especially under cyclic loading conditions inherent in a patient's circulatory system. The strain induced during deployment can result in significant loss in radial strength.

In light of the foregoing, there is a need for a stent pattern and manufacturing method that reduces the cracks and other defects due to crimping. There is also a need for a stent pattern and manufacturing method that results in less strain when a stent is deployed for implantation.

SUMMARY OF THE INVENTION

Briefly and in general terms, the present invention is directed to a stent and a method of manufacturing a stent.

In aspects of the invention, a method comprises determining a shape of a first stent scaffold radially compressed to a reduced outer diameter, the stent scaffold capable of being deployed to an expanded outer diameter. The method further comprises determining a pattern from the determined shape. The method further comprises fabricating a precursor tube by extruding a substrate polymer including poly L-lactic acid (PLLA), the precursor tube having the reduced outer diameter. The method further comprises forming a second stent scaffold by applying the determined pattern to a the precursor tube, the second stent scaffold capable of being deployed to the expanded outer diameter.

In aspects of the present invention, a method comprises providing a precursor tube made of a substrate polymer including poly L-lactic acid (PLLA). The method further comprises forming a stent scaffold by applying a pattern of struts on the precursor tube, the pattern comprising a plurality of serpentine rings that define closed cells, each closed cell bounded by struts that are partly linear, bending elements, and links, wherein the serpentine rings are defined by the partly linear struts and the bending elements, the links connecting each one of the serpentine rings to another one of the serpentine rings, the struts oriented in such a way to form interior angles of between 80 degrees and 95 degrees between every two adjacent struts.

In aspects of the invention, a polymeric stent comprises a stent scaffold made of a substrate polymer including poly L-lactic acid (PLLA), the stent scaffold comprising a plurality of struts forming a plurality of rings, each pair of adjacent rings connected to each other by links, there being exactly three closed cells enclosed within each pair of adjacent rings, the struts being oriented in such a way to form interior angles of between 80 degrees and 95 degrees between every two adjacent struts.

The features and advantages of the invention will be more readily understood from the following detailed description which should be read in conjunction with the accompanying drawings.

DETAILED DESCRIPTION OF THE INVENTION

As used herein, "biocompatible" refers to a polymer that both in its intact, as synthesized state and in its decomposed state, i.e., its degradation products, is not, or at least is minimally, toxic to living tissue; does not, or at least minimally and reparably, injure(s) living tissue; and/or does not, or at least minimally and/or controllably, cause(s) an immunological reaction in living tissue.

As used herein, the terms "bioabsorbable," "biodegradable," and "absorbed," are used interchangeably (unless the context shows otherwise) and refer to materials that are capable of being degraded or absorbed when exposed to bodily fluids such as blood, and components thereof such as enzymes, and that can be gradually resorbed, absorbed, and/or eliminated by the body.

The words "substantially" or "substantial" as used herein to modify a condition means that the condition is present in absolute or perfect form, as well as in a form that is not necessarily absolute or perfect but would be considered close enough to those of ordinary skill in the art to warrant designating the condition as still being present.

Figure 1:
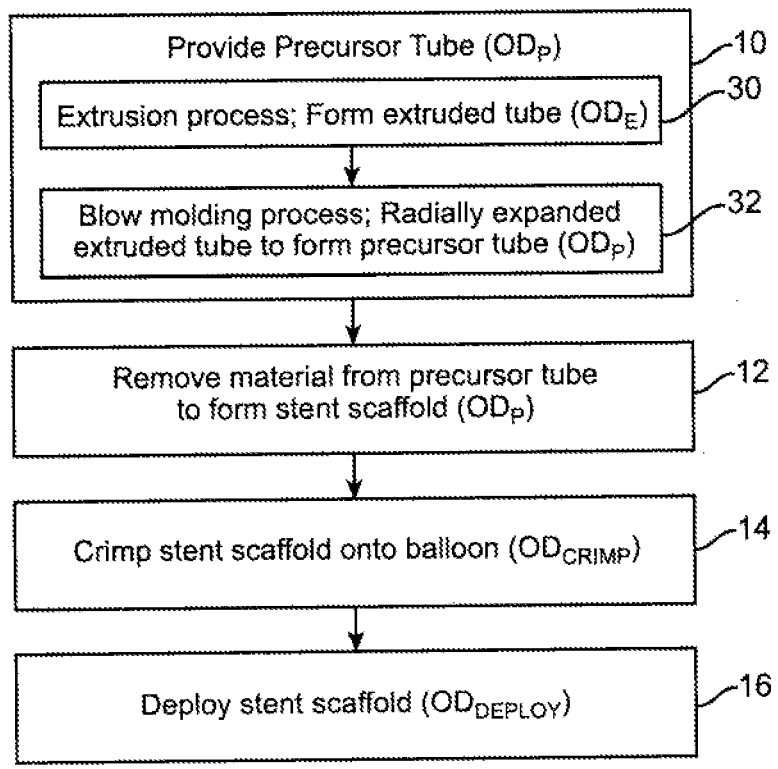
FIG. 1 is a flow chart showing a process for manufacturing a polymeric stent scaffold from a precursor tube followed by deployment of the stent scaffold.

FIG. 1 depicts a method for making and deploying a stent. The method includes providing 10 a precursor tube of solidified polymer material, removing 12 material from the precursor tube to form a stent scaffold, crimping 14 the stent scaffold onto a balloon, then expanding 16 the stent scaffold to a deployed state. Expansion 16 of the stent scaffold is performed by inflating the balloon after the stent scaffold has been positioned at the desired position within the patient.

Figure 2:
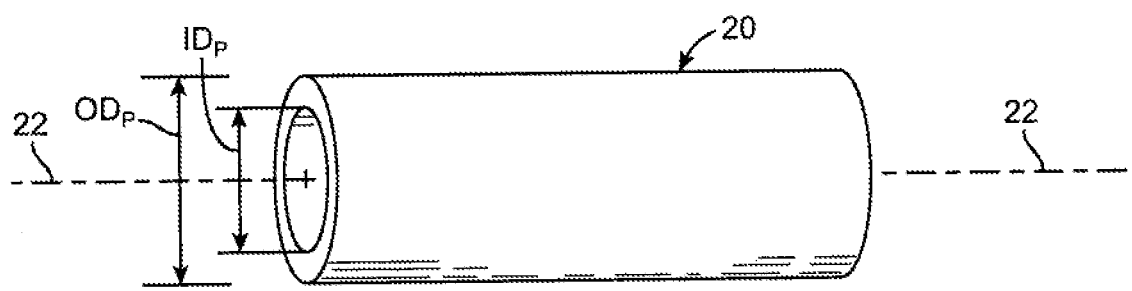
FIG. 2 is a perspective view of a precursor tube.
Figure 3:
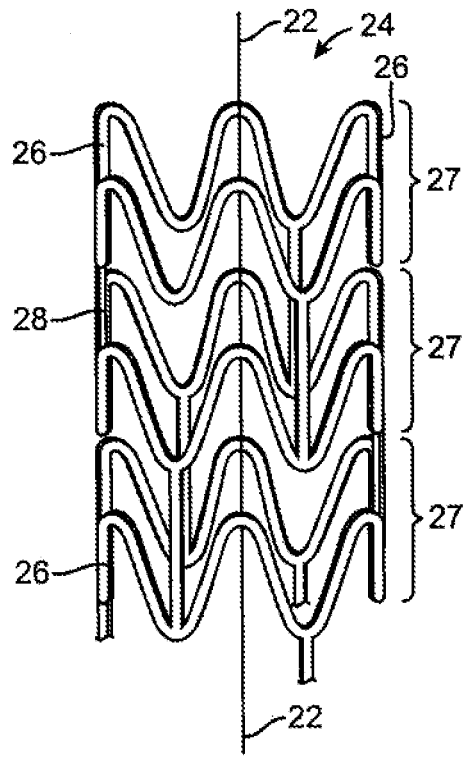
FIG. 3 is a perspective view of a stent scaffold.

An exemplary precursor tube is shown in FIG. 2. The precursor tube 20 has a central axis 22, an inner diameter $ID_P$, and an outer diameter $OD_P$. The precursor tube 20 is made of a biocompatible polymer intended to form the core material or substrate of the stent scaffold. The phrase "substrate" refers to the material at the core of the structural element of the stent scaffold and does not include any coatings of other material deposited after formation of the stent scaffold. A segment of a conventional stent scaffold 24 is shown in FIG. 3. The stent scaffold 24 includes a plurality of struts 26 which form a plurality of ring structures 27 connected to each other by links 28. The ring structures are configured to collapse during crimping and expand during deployment. The central axis 22 of the stent scaffold corresponds to that of the precursor tube 20.

As used herein "substrate polymer" refers to the polymer used to make the precursor tube 20. The substrate polymer can be bioabsorbable. Bioabsorbable polymers include without limitation poly(lactic-co-glycolic acid) (PLGA) and poly(L-lactic acid) (PLLA). PLLA is a monomer and PLGA is a co-polymer in which the percentage of glycolic acid (GA) may vary. PLLA and PLGA are semi-crystalline polymers in that their morphology includes crystalline and amorphous regions, though the amount of crystallinity can be altered to provide the desired combination of mechanical properties of the stent scaffold, such as flexibility to allow for crimping, toughness or resistance to fracture during crimping and deployment, and rigidity to support surrounding anatomical tissue after deployment. Other suitable polymers include without limitation poly(L-lactide-co-D-lactide) ("PLLA-co-PDLA"), poly(L-lactic acid)/poly(D-lactic acid) ("PLLA/PDLA") stereocomplex, and PLLA-based polyester block copolymer containing a rigid segment and a soft segment, the rigid segment being PLLA or PLGA, the soft segment being poly(ε-caprolactone) ("PCL") or poly(trimethylene carbonate) ("PTMC"). Other suitable substrate polymers and particular compositions for PLLA and PLGA include those described in commonly assigned U.S. patent application Ser. No. 12/558,105, entitled, "Polymeric Stent and Method of Making Same", filed Sep. 11, 2009, which is incorporated herein by reference.

The precursor tube 20 is made by an extrusion process 30 and blow molding process 32 (FIG. 1). In the extrusion process 30, the substrate polymer is fed into an extruder. In the extruder the substrate polymer is melted at a controlled temperature and a controlled pressure, then forced through an annular die to form an extruded tube. The extrusion process 30 can be as described in U.S. Pub. No. 20060020330, which is incorporated herein by reference.

Presently, preferred dimensions for the extruded tube, when solidified, are as follows. A PLLA extruded tube having 0.025 inch ID and 0.066 inch OD is radially expanded to make a 3.5 mm precursor tube. A PLLA extruded tube having 0.021 inch ID and 0.064 inch OD is radially expanded to make 3.0 mm OD precursor tube. A PLLA extruded having 0.17 inch ID and 0.054 inch OD is radially expanded to make a 2.5 mm OD precursor tube. The abbreviation "ID" refers to the inner diameter of the tube, and the abbreviation "OD" refers to outer diameter of the tube.

The blow molding process 32 is performed on the extruded tube to form a precursor tube with a desired combination of dimensions and mechanical properties. The blow molding process 32 induces orientation in molecular polymer chains. The blow molding process 32 comprises placing the extruded tube into a glass tubular mold in which the extruded tube is heated to a controlled temperature. A gas is pumped into the extruded tube to achieve a controlled internal pressure which causes the extruded tube to radially expand within the tubular mold. Radial expansion occurs at a segment of the extruded tube where heat is concentrated by a nozzle blowing heated gas onto an outer surface of the tubular mold. Because the heating device travels along the axial length of the extruded tube at a controlled rate of travel, radial expansion occurs in a progressive fashion, starting from one end of the extruded tube and progressing toward the opposite end of the extruded tube, such as described in U.S. Publication Nos. 20090001633 and 20090146348, which are incorporated herein by reference. The process parameters, such as heating temperature, pressure, rate of travel of the heating device, can be as described in U.S. patent application Ser. No. 12/558,105, entitled, "Polymeric Stent and Method of Making Same", filed Sep. 11, 2009, which is incorporated herein by reference, and in U.S. Pub. No. 20090146348. These process parameters and other processing conditions can also be as described in U.S. Pub. No. 20100025894, which is incorporated herein by reference. Upon completion of radial expansion, the resulting tube is cooled or allowed to cool, then removed from the tubular mold for use as the precursor tube 20.

The tubular mold has a predetermined inner diameter which corresponds to the desired outer diameter $OD_P$ of the precursor tube 20 and the outer diameter of the stent scaffold which is made from the precursor tube. The desired outer diameter of the precursor tube is carefully selected because it directly determines the amount of radial expansion as well as the amount and direction of molecular polymer chain orientation that will be induced during the blow molding process 32, which in turn affect the mechanical properties of the stent scaffold.

There are several interrelated and competing considerations for choosing the outer diameter $OD_P$ of the precursor tube 20. As previously indicated, $OD_P$ also corresponds to the outer diameter of the stent scaffold immediately after its formation by removal 12 of material from the precursor tube 20.

One consideration for choosing the outer diameter $OD_P$ of the precursor tube is the hoop strength of the stent scaffold. Hoop strength enables the stent scaffold to withstand radial compressive forces from the surrounding anatomical lumen after deployment within a patient. Hoop strength could be increased by choosing $OD_P$ that is substantially larger than the outer diameter $OD_E$ of the extruded tube at the start of blow molding process. If $OD_P$ is small and close in size to $OD_E$, the molecular polymer chain orientation in the circumferential direction that is induced during the blow molding process may be insufficient to prevent the stent scaffold from partially collapsing radially inward (referred to as "recoil") or from totally collapsing after deployment. Hoop strength could also be increased by choosing $OD_P$ that is close to the intended deployed diameter $OD_{DEPLOY}$ of the stent scaffold. If $OD_P$ is too small in relation to $OD_{DEPLOY}$, shape memory, due to plastic deformation or despite plastic deformation during deployment, may be such that the stent scaffold recoils inward or contracts slightly immediately or soon after deployment. Also, an overly small $OD_P$ in relation to $OD_{DEPLOY}$ may result in fracture due to strain caused by balloon expansion that forces the stent scaffold to the deployed diameter $OD_{DEPLOY}$. Post-deployment recoil or fractures could result in loss of patency of the anatomical lumen being treated.

Another consideration for choosing the outer diameter $OD_P$ of the precursor tube is flexibility to allow the stent scaffold to be crimped to the desired crimp diameter $OD_{CRIMP}$. Flexibility is also needed to enable movement and positioning of the stent scaffold within tortuous and tight spaces within the anatomy prior to deployment. Flexibility can be enhanced by choosing $OD_P$ that is close to the outer diameter $OD_E$ of the extruded tube at the start of blow molding process. If the $OD_P$ is too large in relation to the $OD_E$, the molecular polymer chain orientation in the circumferential direction that is induced during the blow molding process may make the stent scaffold too stiff or rigid, resulting in fractures. The ability of the stent scaffold to be crimped can be enhanced by choosing $OD_P$ that is close to the desired crimp diameter as $OD_{CRIMP}$. An overly large $OD_P$ in relation to $OD_{CRIMP}$ would cause more flexure of the stent scaffold during crimping, which corresponds to more strain during crimping that can compromise structural integrity. Also, if the $OD_P$ is too large in relation to $OD_{CRIMP}$, elastic shape memory, due to plastic deformation or despite plastic deformation during crimping, may be such that the stent scaffold springs outward or expands slightly immediately or soon after crimping. Post-crimping expansion and fractures can compromise retention of the stent scaffold on the delivery balloon and can compromise the functional life of the stent scaffold. Thus, it should be understood that considerations for selecting of $OD_P$ of the precursor tube are varied and complex.

Figure 4:
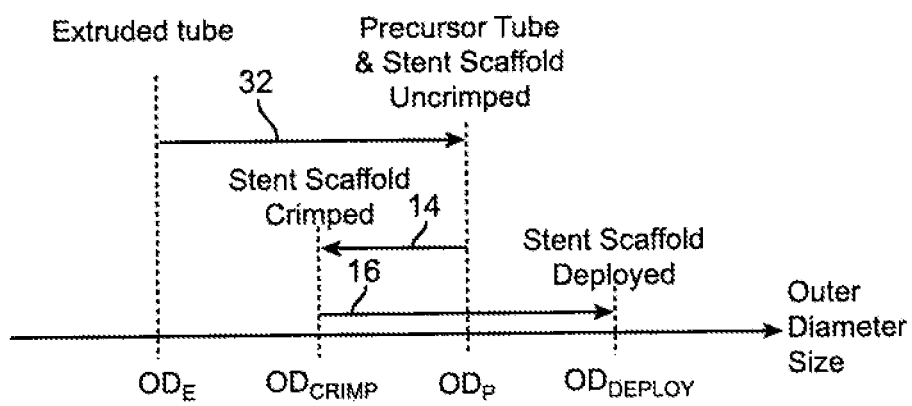
FIG. 4 is flow chart showing the relative outer diameter sizes during the process of manufacturing the stent scaffold according to FIG. 1.

A preferred size relationship of the above described outer diameters is shown in FIG. 4 which is not drawn to scale. The outer diameter $OD_E$ of the extruded tube is the smaller than the outer diameter $OD_P$ of the precursor tube. The deployed diameter $OD_{DEPLOY}$ of the stent scaffold is greater than the initial diameter $OD_P$ of the stent scaffold. The crimped diameter $OD_{CRIMP}$ of the stent scaffold is less than $OD_E$. In other embodiments, $OD_P$ and $OD_{DEPLOY}$ are the substantially the same.

Yet another consideration for choosing the outer diameter $OD_P$ of the precursor tube is the geometric pattern applied to the precursor tube to make the stent scaffold. The pattern must be able to collapse from $OD_P$ to the requisite crimp diameter $OD_{CRIMP}$ and expand to $OD_{DEPLOY}$, as shown in FIG. 4.

Figure 5:
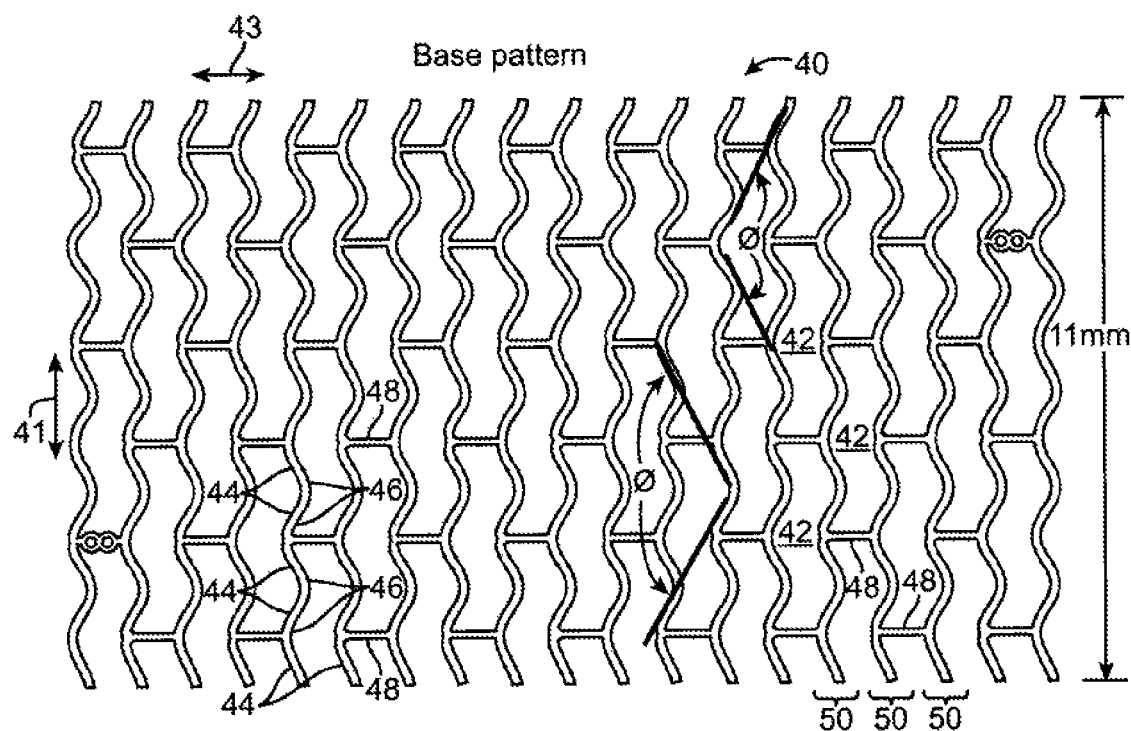
FIG. 5 is a plan view of a pattern of struts to be applied to a precursor tube to form a stent scaffold.
Figure 6:
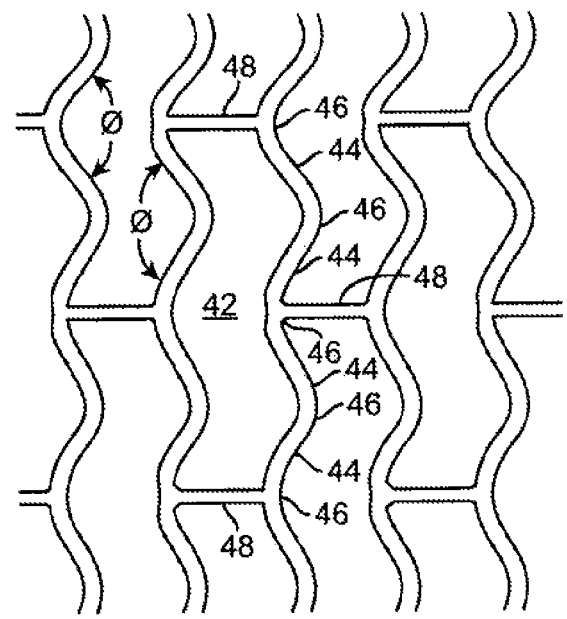
FIG. 6 is a detailed view of a portion of the pattern of FIG. 5.

FIG. 5 shows an example of a geometric pattern 40 applied to a precursor tube to make a stent scaffold. The pattern 40 is designed to collapse from $OD_P \approx 3.5$ mm to crimp diameter $OD_{CRIMP} \approx 1.3$ mm and expand to $OD_{DEPLOY} \approx 3.8$ mm ($ID_{DEPLOY} \approx 3.5$ mm). As used herein, the "≈" symbol means "substantially equal to." The pattern 40 is the same as the pattern described in connection with FIGS. 4-9 of U.S. Pub. No. 20080275537, which is incorporated herein by reference. FIG. 6 shows a detail view of a portion of FIG. 5. The pattern 40 is of interconnected structural elements which form a regularly repeating arrangement of W-shaped closed cells 42 that are offset from each other in brick design. The structural elements include substantially linear struts 44, bending elements 46, and substantially linear links 48.

The pattern of FIG. 5 is shown in a planar or flat state, although the pattern is actually in tubular form when cut onto the precursor tube. The bottom edge of the pattern in FIG. 5 actually meets with and is connected to the top edge of the pattern so as to form the tubular body of the stent scaffold. Thus, it will be appreciated that the linear struts, when formed on the precursor tube 20, form a plurality of serpentine rings 50 that encircle the central axis of the stent scaffold. The rings 50 are connected to each other by the links 48 which are substantially parallel to the central axis of the stent scaffold. The struts 44 are interconnected end-to-end by the bending elements 46 to form the rings 50. The rings 50 are arranged axially to form the tubular body of the stent scaffold. The struts 44 are configured to have sufficient rigidity that provides the rings 50 with the hoop strength needed after deployment. The bending elements 46 are configured to have sufficient flexibility to provide the rings 50 with the ability to be crimped and deployed without sustaining significant structural damage. The links 48 are configured to have sufficient flexibility that provides the stent scaffold with the ability to bend and pass through tortuous passageways within the anatomy prior to deployment. It should also be understood that the choice of material for the stent scaffold substrate also affects hoop strength and flexibility.

The geometric pattern 40 can be applied to the precursor tube 20 by inputting the pattern into a CAD/CAM software program that generates a laser cut routine which is then used to cut and remove material from the precursor tube 20. The pattern 40 can be cut onto the precursor tube 20 by a laser cutting process, such as described in U.S. Pub. Nos. 20070034615 and 20070151961, both of which are incorporated herein by reference.

The selected outer diameter $OD_P$ of the precursor tube 20 affects the amount of radial expansion from $OD_E$, which in turn affect the mechanical properties of the individual struts, bending elements, and links of the resulting stent scaffold. The mechanical properties of these individual structural elements are also affected by the orientation of the individual structural elements. Due to radial expansion and the resulting molecular orientation of polymer chains induced during the blow molding process, structural elements are expected to be stiffer in the circumferential direction (vertical arrow 41 in FIG. 5) than in the axial orientation (horizontal arrow 43 in FIG. 5). In combination with orientation of the individual structural elements, stiffness and flexibility among the structural elements will depend upon the amount of radial expansion that occurs during the blow molding process 32, which depends directly on the chosen outer diameter $OD_P$ of the precursor tube.

Referring again to FIG. 5, the pattern 40 is to be applied to the precursor tube 20 for making a stent scaffold. The pattern has a circumferential dimension, from the bottom edge to the top edge, of about 11 mm and more narrowly 10.89 mm, which corresponds to the circumference of the outer diameter $OD_P=3.5$ mm of the precursor tube. The pattern 40, details of which are discussed further below, is designed to allow the stent scaffold to be crimped to an outer diameter $OD_{CRIMP}$ of about 1.3 mm and radially expanded to at least an inner diameter $ID_{DEPLOY}$ of about 3.5 mm and outer diameter $OD_{DEPLOY}$ of about 3.8 mm.

As previously discussed, a problem with polymeric stents is that they can fracture during crimping and deployment. Non-uniform collapse of struts during crimping can also be a problem. In the case of the pattern of FIG. 5 as applied to a precursor tube having $OD_P=3.5$ mm, the fractures and/or non-uniform collapse that develop are of sufficient number and/or are located at particular regions of the stent scaffold to warrant rejection of 24% to 30% of stent scaffolds manufactured. One way to reduce the incidence of fractures during crimping might be to cut the pattern onto a precursor tube having a reduced outer diameter that is smaller than $OD_P$ and closer in size to $OD_{CRIMP}$. Having a reduced outer diameter, denoted $OD_{PR}$, that is closer to $OD_{CRIMP}$ will reduce the amount of flexure and deformation that the stent scaffold must undergo during the crimping process 14 to achieve $OD_{CRIMP}$. However, as discussed above, reducing the outer diameter of the precursor tube will increase the amount of flexure and deformation that the stent scaffold must undergo during the deployment process 16 to achieve $OD_{DEPLOY}$. Also, reducing the outer diameter of the precursor tube, without also reducing the outer diameter $OD_E$ of the extruded tube, will decrease the amount of radial expansion of the extruded tube that occurs during the blow molding process to make the precursor tube, and such reduction affects the amount and direction of molecular polymer chain orientation induced, which in turn affects mechanical properties of the resulting stent scaffold.

The pattern of FIG. 5 is too large in the circumferential direction to fit on a precursor tube with a reduced outer diameter $OD_{PR}$, so the pattern must first be modified. As previously indicated, the pattern 40 has a circumferential dimension, from the bottom edge to the top edge, of about 11.0 mm which corresponds to $OD_P=3.5$ mm. A precursor tube with a reduced outer diameter $OD_{PR}=3.0$ mm will have an outer circumference of about 9.4 mm. Thus, the pattern 40 is about 1.6 mm too large in the circumferential direction to be applied to a precursor tube with $OD_{PR}=3.0$ mm.

Figure 7A:
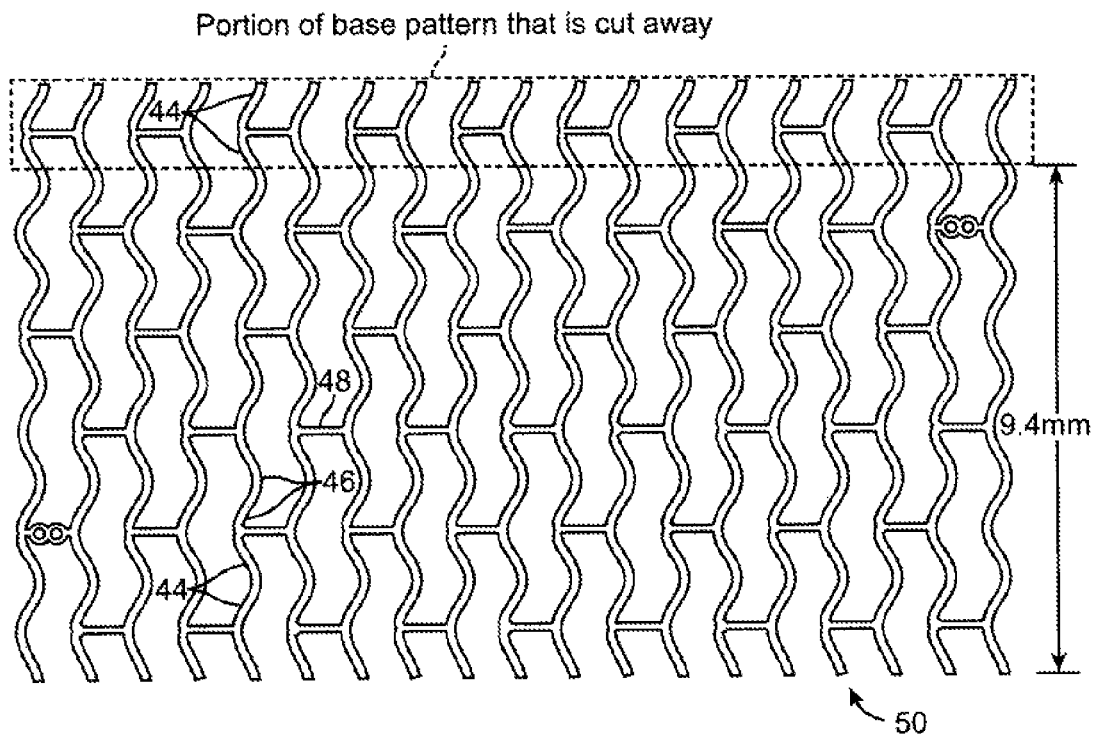
FIG. 7A-7C are plan views of different patterns derived from the base pattern of FIG. 5, the derived patterns to be used to form stent scaffolds from precursor tubes having a reduced outer diameter for the purpose of reducing the incidence of defects during crimping.

Various approaches can be taken to adjust the pattern 40 of FIG. 5 for application with a precursor tube having reduced outer diameter $OD_{PR}=3.0$ mm. One approach is to cut 1.6 mm from the pattern, as shown in FIG. 7A, to produce a pattern 50 with a 9.4 mm circumferential dimension that matches a precursor tube with $OD_{PR}=3.0$ mm. A problem with this approach is that the structural elements at the bottom edge of the resulting pattern 50 in FIG. 7A will not meet with those at the top edge. Also, removal of some of the stent struts 44 (in the box illustrated in broken line) means that there will be fewer remaining struts to support the surrounding anatomical lumen after deployment in a patient. Removal of some of the struts 44 will also prevent the stent scaffold from being deployed to the same extent as the base pattern 40 of FIG. 5.

Figure 7B:
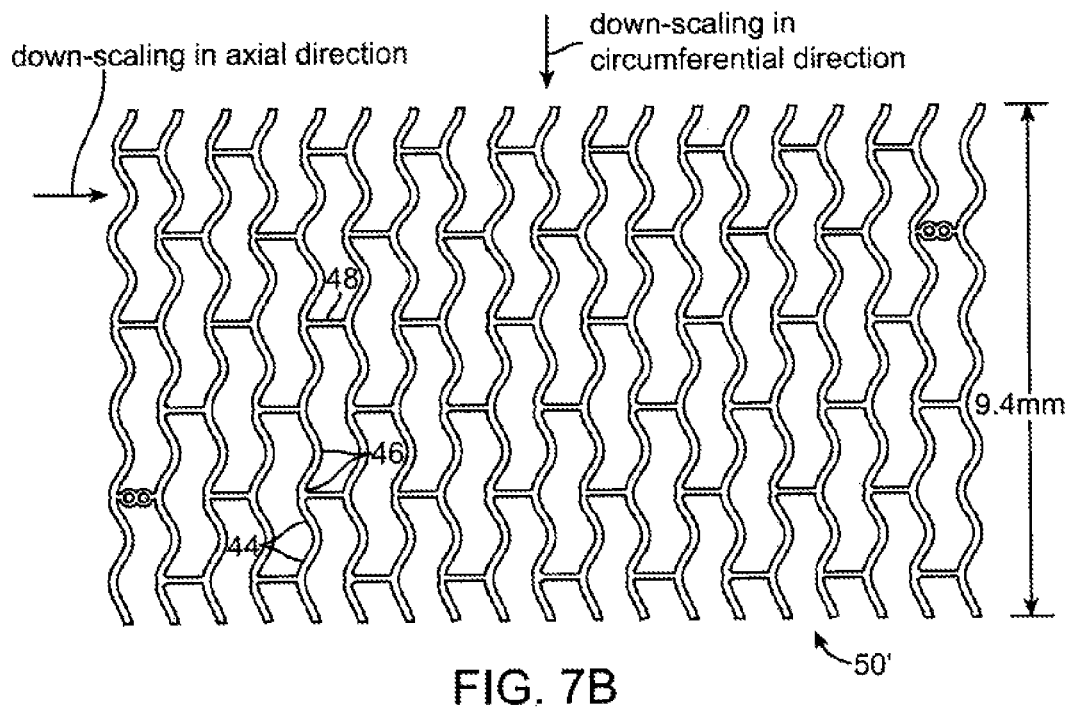

Another approach for adjusting the pattern 40 of FIG. 5 for application with a precursor tube having $OD_{PR}$ less than 3.5 mm is to scale down the pattern 40 so that it has a circumferential dimension that corresponds with the reduced diameter. For example, the pattern 40 can be scaled down, as shown in FIG. 7B, to produce a pattern 50' with a 9.4 mm circumferential dimension that matches a precursor tube with $OD_{PR}=3.0$ mm. A problem with this approach is that the width of the structural elements will also be scaled down, which can make the struts 44 insufficiently rigid and make the bending elements 46 and links 48 overly flexible. Also, the total length of the stent will be reduced. Another shortcoming is that the length of the struts 44 and links 48 will also be scaled down, which can prevent the stent scaffold from being deployed to the same extent as the base pattern 40 of FIG. 5.

Figure 7C:
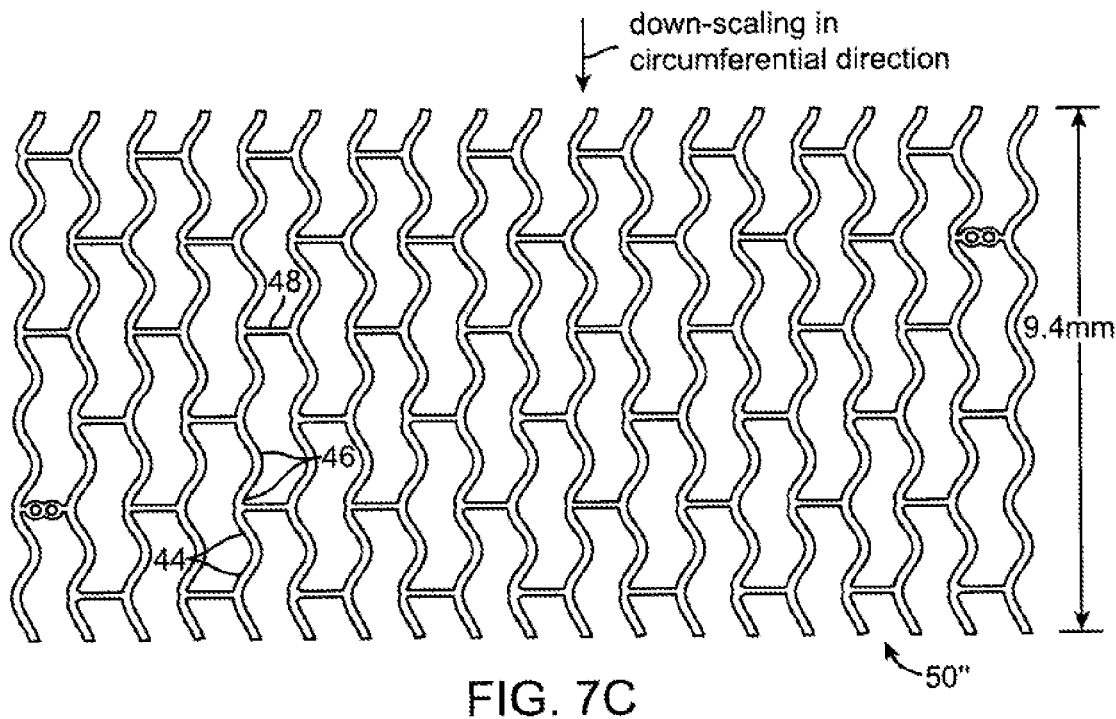

Yet another approach for adjusting the base pattern 40 of FIG. 5 for application with a precursor tube having $OD_{PR}$ less than 3.5 mm is to scale down the pattern 40 in the circumferential direction, as shown in FIG. 7C, without scaling down the pattern in the axial direction. A problem with this approach is that length of the struts 44 in the new pattern 50" will also be scaled down (although to a lesser extent than in FIG. 7B), which can prevent the stent scaffold from being deployed to the same extent as the base pattern 40 of FIG. 5.

Figure 8:
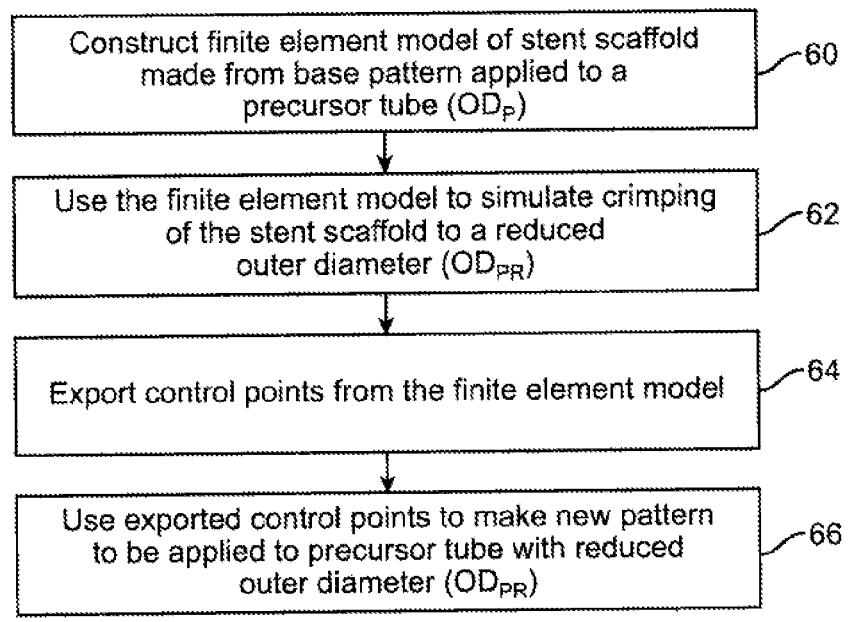
FIG. 8 is a flow chart showing a process for deriving a new pattern from a base pattern by predicting the shape of a stent scaffold that has been radially compressed to a reduced diameter, the derived pattern to be used to form a stent scaffold from a precursor tube having the reduced diameter for the purpose of reducing the incidence of fractures during crimping.

Applicant has found that a better approach for adjusting the base pattern 40 of FIG. 5 for application with a precursor tube having $OD_{PR}$ less than 3.5 mm is to use a method, as shown in FIG. 8, to predict the shape of the stent scaffold at $OD_{PR}$ and then use the predicted shape to design a new pattern that is applied to a precursor tube with an outer diameter of $OD_{PR}$. The pattern 40 of FIG. 5 is referred to as a base pattern from which the new pattern is to be derived. The prediction step comprises constructing 60 a three-dimensional computer or numerical model of the stent scaffold made with the base pattern 40 of FIG. 5 applied to a precursor tube with $OD_P=3.5$ mm. The model is referred to as a finite element model because it comprises a plurality of discrete elements or blocks arranged in the shape of the actual stent scaffold. Finite element modeling methods are known in the art, so details need not be described in detail herein. Generally, the model includes mathematical equations that characterize how the discrete elements can deform and/or move relative to each other. A plurality of control points on the model are selected for tracking purposes. Next, the model is used to simulate 62 crimping of the stent scaffold to a reduced outer diameter $OD_{PR}$. The changed position of the control points are exported 64, then used 66 to design a new pattern that can be applied onto a precursor tube of reduced outer diameter $OD_{PR}$. In this way, the new pattern matches the control points for the precursor tube of $OD_{PR}$. The new pattern is inputted to a CAD/CAM software to generate a laser cut routine that is applied to the precursor tube of $OD_{PR}$.

Figures 9, 10:
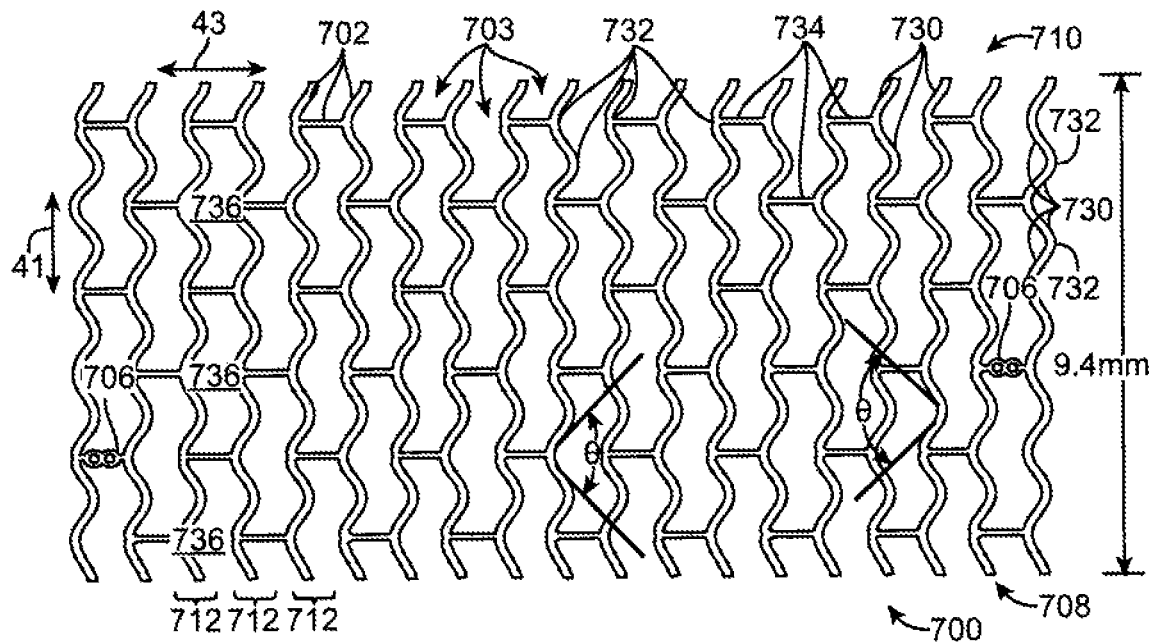
FIG. 9 is a plan view of a new pattern derived from the base pattern of FIG. 5 according to the method described in connection with FIG. 8.
FIG. 10 is a graph showing the number of stent scaffolds rejected due to fracture during crimping, and showing a reduction in the number of rejects for stent scaffolds of the new pattern of FIG. 9 as compared to the base pattern of FIG. 5.

FIG. 9 shows a new pattern 700 for use with a precursor tube having $OD_{PR}=3.0$ mm. The new pattern 700 was derived according to the method of FIG. 8 from the base pattern 40 of FIG. 5 for $OD_P$=3.5 mm. Like the new patterns 50, 50', 50" of FIGS. 7A-7C, the new pattern 700 of FIG. 9 has a circumferential dimension of 9.4 mm. However, unlike the new patterns of FIGS. 7A-7C, the new pattern 700 is capable of expanding to the same extent as the base pattern 40 of FIG. 5 since no struts were removed and since the length of the struts are substantially unchanged. Over a hundred PLLA stent scaffolds were made with the new pattern 700 cut onto a precursor tube with $OD_{PR}$=3.0 mm. Each scaffold had outer diameter of 3.0 mm. The stent scaffolds were then crimped and inspected for fractures and other crimp defects, such as non-uniform collapse of struts. Applicant found that, when using the same standard of inspection applied to the base pattern 40 of FIG. 5 applied to PLLA $OD_P$=3.5 mm, the new pattern 700 of FIG. 9 applied to PLLA $OD_{PR}$=3.0 mm yielded 0% rejections. This is a significant reduction in rejects, as shown in FIG. 10.

Figure 11A:
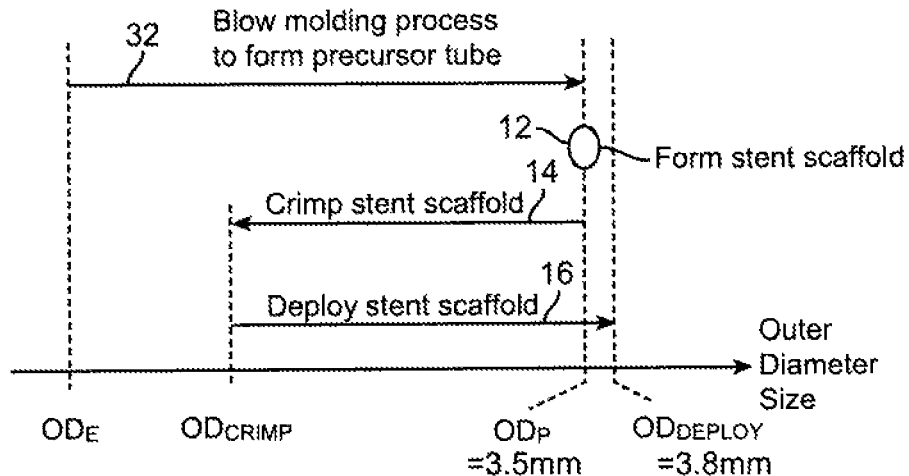
FIGS. 11A and 11B are flow charts showing a process of manufacturing stent scaffolds using the base pattern of FIG. 5 and the new pattern of FIG. 9, respectively.
Figure 11B:
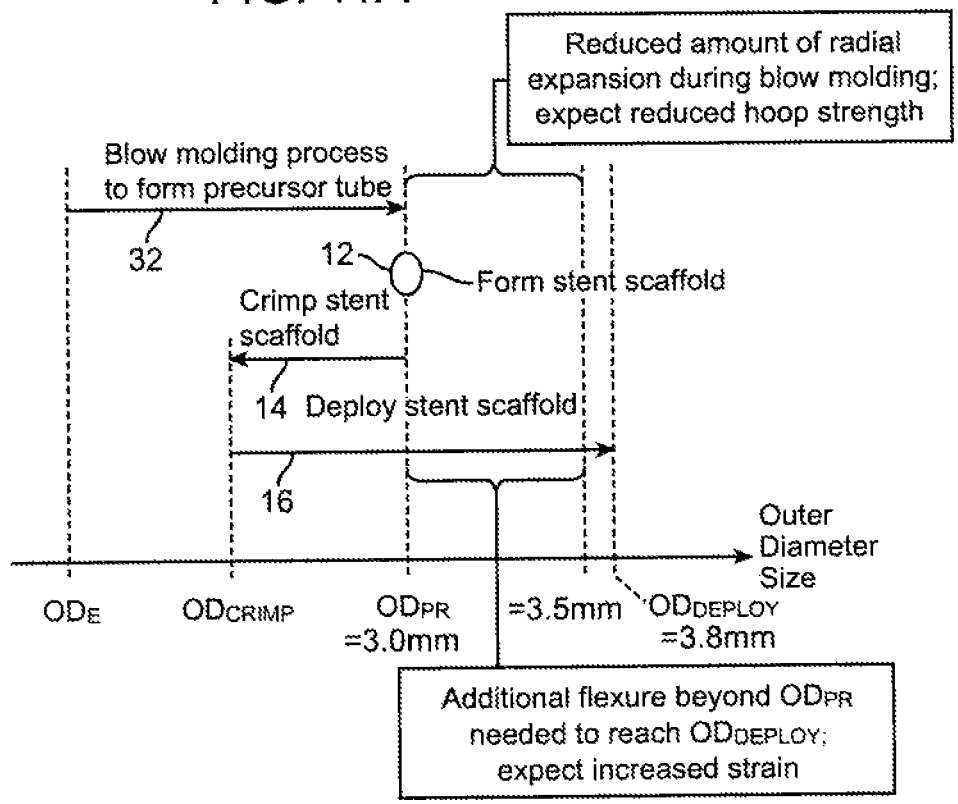

As indicated above, a reduction in the outer diameter of the precursor tube can be expected to increase the amount of strain experienced by the bending elements of the stent scaffold during deployment because of the need for increased flexure. The need for increased flexure is illustrated in FIGS. 11A and 11B, which are not drawn to scale. FIG. 11A shows the process for the base pattern 40 of FIG. 5 applied to $OD_P$=3.5 mm, and FIG. 11B shows the process for the new pattern 700 of FIG. 9 applied to $OD_{PR}$=3.0 mm. Comparison of FIGS. 11A and 11B indicates that the bending elements of the stent scaffold made with the new pattern 700 will have to flex beyond its original diameter of $OD_{PR}$ to reach the deployment diameter $OD_{DEPLOY}$ of 3.8 mm, which suggests that strain experienced by the stent scaffold should increase with the new pattern 700. However, Applicant has unexpectedly found that strain decreases with the new pattern.

Figure 12A:
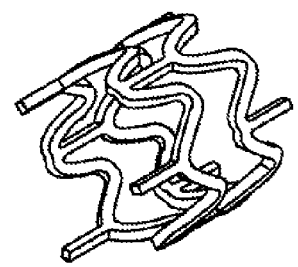
FIGS. 12A-12C are isometric views of finite element models of stent scaffolds using: (A) a new pattern applied to a precursor tube having a 2.5 mm outer diameter, (B) the new pattern of FIG. 9 applied to a precursor tube having a 3.0 mm outer diameter, and (B) the base pattern of FIG. 5 applied to a precursor tube having a 3.5 mm outer diameter.
Figure 12B:
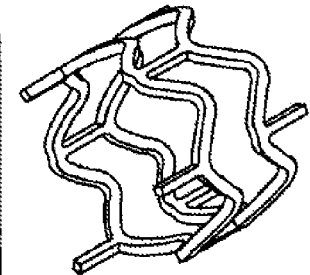
Figure 12C:
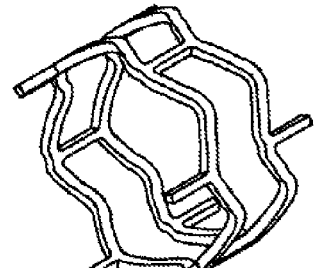
Figure 13A:
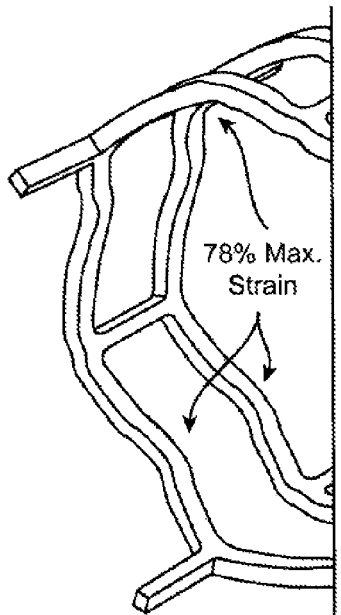
FIGS. 13A-13C are isometric views of the finite element models of FIGS. 12A-12C after simulating deployment to an outer diameter of 3.5 mm.
Figure 13B:
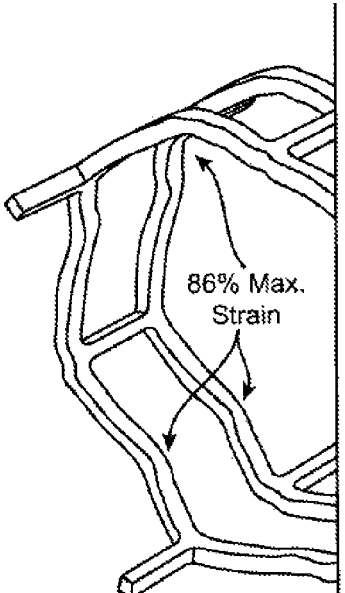
Figure 13C:
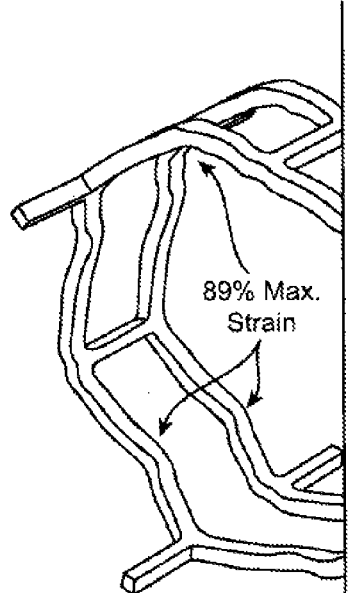

FIGS. 12A-12C show finite element models of respective axial segments of the stent scaffolds made from a new pattern applied to $OD_{PR}$=2.5 mm (FIG. 12A), the new pattern 700 of FIG. 9 applied to $OD_{PR}$=3.0 mm (FIG. 12B), and the base pattern 40 of FIG. 5 applied to $OD_P$=3.5 mm (FIG. 12C). The new patterns for $OD_{PR}$ of 2.5 mm and 3.0 mm are different from each other, and were separately derived from the base pattern 40 according to the method described in connection with FIG. 8. FIGS. 13A-13C show the same finite element models simulating deployment to $ID_{DEPLOY}$=3.5 mm, which corresponds to $OD_{DEPLOY}$ of about 3.8 mm. The simulations show the location of greatest strain in the stent scaffold to be at the bending elements.

TABLE 1 and FIGS. 13A-13C show the maximum strain at $OD_{DEPLOY}$~3.8 mm, as a percentage of the strain that will result in fracture. For the base pattern of FIG. 3 applied to $OD_P$=3.5 mm, the maximum strain at $OD_{DEPLOY}$~3.8 mm is 89%. The maximum strain is lower for the new patterns (derived from the base pattern according to the method of FIG. 8) applied to precursor tubes having reduced outer diameters $OD_{PR}$ of 3.0 mm and 2.5 mm. This decrease is unexpected. As previously explained in connection with FIGS. 11A and 11B, it was expected that strain at deployment would be higher with the smaller precursor tubes because the smaller precursor tubes would have to expand beyond their original diameter to reach the deployment diameter.

TABLE 1

| Precursor Tube Outer Diameter | Maximum Strain at Deployment, $OD_{DEPLOY}$~3.8 mm |
|---|---|
| 3.5 mm | 89% (see FIG. 13C) |
| 3.0 mm | 86% (see FIG. 13B) |
| 2.5 mm | 78% (see FIG. 13A) |

In addition to the method of FIG. 8, other methods are contemplated for deriving a new pattern for use on a precursor tube with a reduced outer diameter. Those methods are described below in connection with FIGS. 14-16.

Figure 14A:
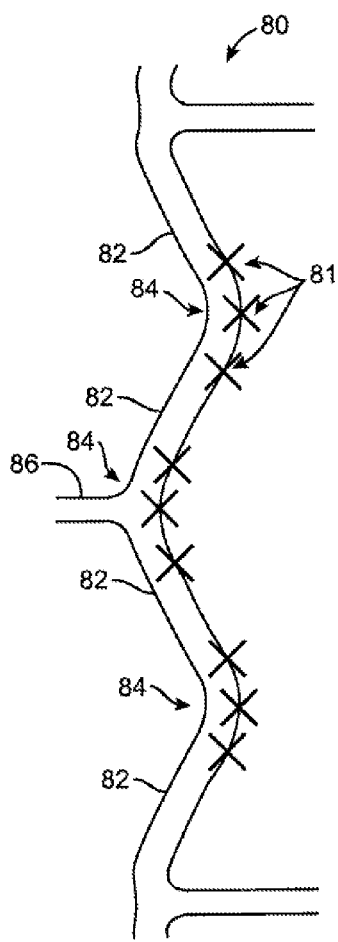
FIGS. 14A-14C are views of sequential steps for a process for deriving a new pattern from a base pattern by tracking changes in position of control points during simulation of radial compression of a stent scaffold.
Figure 14B:
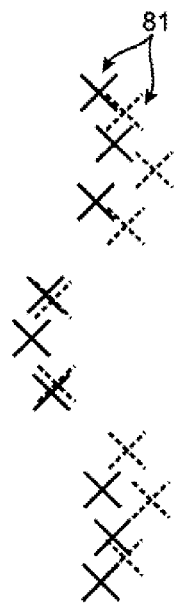
Figure 14C:
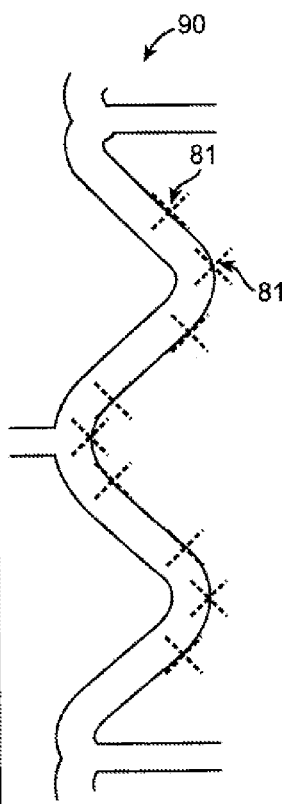

In one exemplary method, as shown in FIG. 14A-14C, a new pattern is derived by constructing a numerical or computerized model 80 of at least a portion of a stent scaffold having an outer diameter $OD_P$ and having a base pattern of struts 82, bending elements 84, and links 86. By taking into account mechanical properties and dimensions of the substrate, the model 80 is designed to allow simulation of radial compression of the actual stent scaffold, such as would occur during crimping. Certain points on the model are designated as control points 81. The control points can correspond to regions of the model which are expected to bend. The control points can correspond to intersection points on the model 80 where the struts 82, bending elements 84, and links 86 meet. The control points 81 are illustrated as X's in FIG. 14A. The control points 81 are located at the edges of the model 80. It will be appreciated that the control points 81 can be located elsewhere on the model 80.

Referring to FIG. 14B, a simulation of radial compression of the stent scaffold is performed on the model 80. The simulation comprises selecting a reduced outer diameter $OD_{PR}$ to which the model 80 will be radially compress. The simulation causes movement of the model's struts 82, bending elements 84, and links 86. As a result, the control points 81 move to new positions. In FIG. 14B, the original positions of the control points 81 (prior to simulation of radial compression) are illustrated with solid-line X's and the new positions of the control points (after simulation of radial compression) are illustrated with broken-line X's. The model 80 is not illustrated in FIG. 14B to clearly show the change in positions.

Referring to FIG. 14C, the new positions of the control points 81 are used to construct a new pattern 90 which corresponds to the predicted shape of the stent scaffold upon radial compression to the reduced outer diameter $OD_{PR}$.

Figure 15:
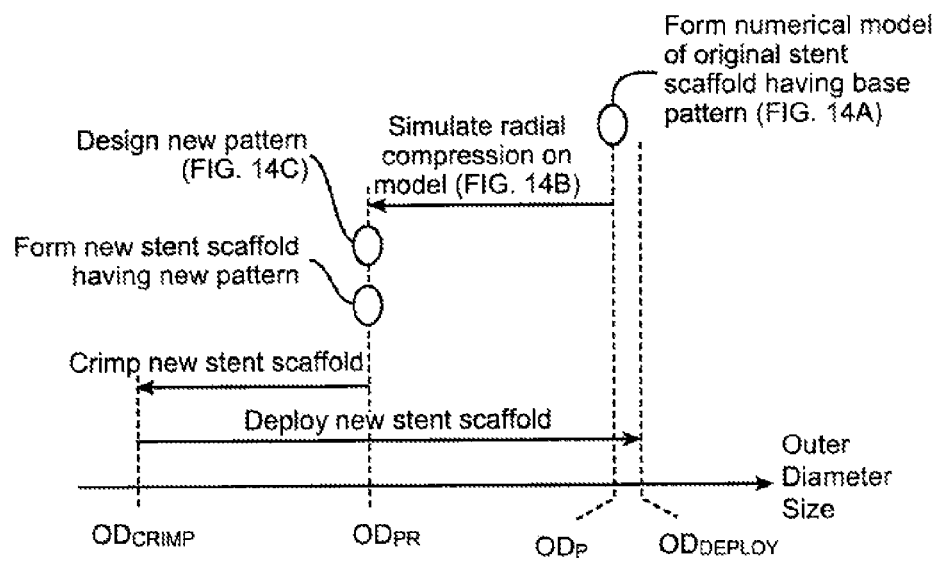
FIG. 15 is a flow chart showing an analytical process for deriving a new pattern from a base pattern by numerically simulating radial compression for an original stent scaffold which is then used to form a new pattern for making a new stent scaffold.

The above analytical process for deriving the new pattern 90 from the base pattern is further illustrated in FIG. 15. It is to be understood that the base pattern and $OD_P$ are such that the original stent scaffold is capable of deploying to an outer diameter $OD_{DEPLOY}$. A new stent scaffold is formed by applying the new pattern 90 on a precursor tube having the reduced outer diameter $OD_{PR}$. The stent scaffold can then be crimped to $OD_{CRIMP}$ onto a delivery balloon and subsequently deployed to $OD_{DEPLOY}$ by inflating the balloon. In FIG. 15, $OD_P$ and $OD_{DEPLOY}$ are not substantially the same. It will be appreciated that, depending on the anatomical lumen being treated, $OD_{DEPLOY}$ can be substantially the same as $OD_E$, $OD_{DEPLOY}$ can be smaller than $OD_E$, or $OD_{DEPLOY}$ can be larger than $OD_E$.

Figure 16:
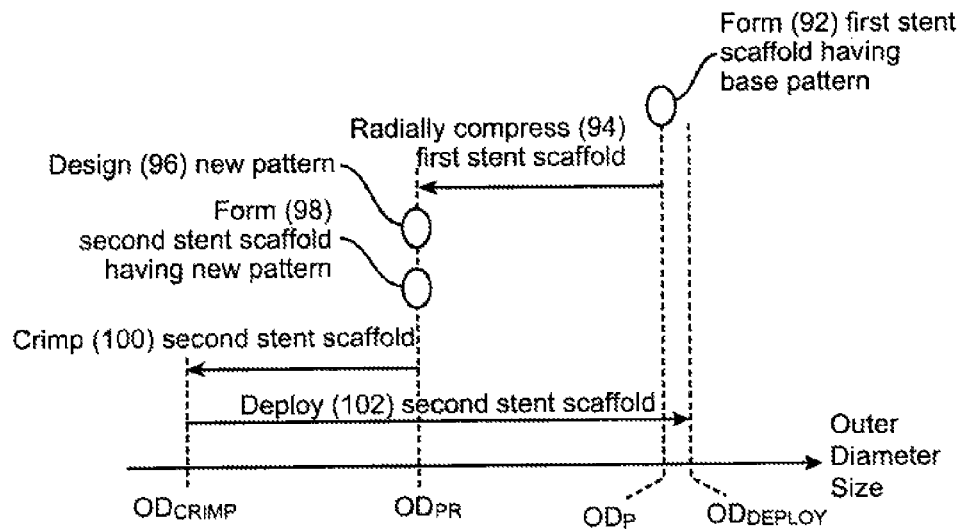
FIG. 16 is a flow chart showing an empirical process for deriving a new pattern from a base pattern by radially compressing a first stent scaffold which is then used to form a new pattern for making a second stent scaffold.

In another exemplary method, as shown in FIG. 16, a new pattern is derived empirically from a base pattern by observing actual radial compression on a stent scaffold. A first stent scaffold is formed 92 by applying a base pattern to a precursor tube having an outer diameter $OD_P$ so that the first stent scaffold also has an outer diameter $OD_P$. The base pattern and $OD_P$ are such that the first stent scaffold is capable of deploying to an outer diameter $OD_{DEPLOY}$. Control points on the first stent scaffold are marked, such as with indelible ink. Next, the first stent scaffold is radially compressed 94 to a reduced outer diameter $OD_{PR}$. The new position of the control points are determined, such as by visual inspection using an optical comparator or a video system. The new position of the control points are used to design 96 a new pattern that corresponds to the actual shape of the first stent scaffold after radially compression to $OD_{PR}$. A second stent scaffold is formed 98 by applying the new pattern on a precursor tube having the reduced outer diameter $OD_{PR}$. The second stent scaffold can then be crimped 100 to $OD_{CRIMP}$ onto a delivery balloon and subsequently deployed 102 to $OD_{DEPLOY}$ by inflating the balloon. In FIG. 16, $OD_E$ and $OD_{DEPLOY}$ are not substantially the same. It will be appreciated that, depending on the anatomical lumen being treated, $OD_{DEPLOY}$ can be substantially the same as $OD_P$, $OD_{DEPLOY}$ can be smaller than $OD_P$, or $OD_{DEPLOY}$ can be larger than $OD_P$.

The new pattern 700 of FIG. 9 will now be described in greater detail. As previously indicated, the new pattern 700 was derived from the base pattern 40 of FIG. 5 according to the method of FIG. 8, and was shown to have improved toughness or fracture resistance during crimping. It is contemplated that the new pattern 700 and other patterns can also be derived according to the method described above in connection with FIGS. 14A-14C, 15 and 16.

The pattern 700 includes various structural elements 702 oriented in different directions and gaps 703 between the structural elements. Each gap 703 and the structural elements 702 immediately surrounding the gap 703 defines a W-shaped closed cell 736. At the proximal and distal ends of the stent, a strut 706 includes depressions, blind holes, or through holes adapted to hold a radiopaque marker that allows the position of the stent inside of a patient to be determined. All the cells 736 have substantially the same size and shape.

The pattern 700 is shown in a planar or flat state, although the pattern is actually in tubular form when cut onto a precursor tube. The bottom edge 708 of the pattern actually meets with and is connected to the top edge 710 of the pattern so as to form the tubular body of the stent scaffold. In this way, the pattern 700 forms sinusoidal hoops or rings 712 that include a group of struts arranged circumferentially. The rings 712 include a series of crests and troughs that alternate with each other. The sinusoidal variation of the rings 712 occurs primarily in the axial direction, not in the radial direction so that all points on the outer surface of each ring 712 are at substantially the same radial distance away from the central axis of the stent.

The rings 712 are connected to each other by substantially linear links 734. The rings 712 are capable of being collapsed to a smaller diameter during crimping and expanded to their original diameter or to a larger diameter during deployment. In other embodiments, the pattern may have a different number of rings 712. The number of rings 712 may vary depending on the desired axial length of the stent.

Referring again to FIG. 9, the rings 712 include substantially linear struts 730 and curved bending elements 732. The struts 730 are connected to each other by the bending elements 732. The bending elements 732 are adapted to flex, which allows the rings 712 to be radially compressed and radially expanded.

It is to be understood that the pattern 700 corresponds to a stent scaffold which has not been crimped or otherwise deformed from its original outer diameter, wherein the outer diameter is that of the precursor tube used to make the stent scaffold. The angles described below for the pattern 700 also apply to the stent scaffold in the non-deformed state before any crimping and before any expansion by a delivery balloon.

The struts 730 are oriented at an interior angle θ relative to each other. The interior angle θ is no greater than 100 degrees. Preferably, the interior angle θ is from about 75 degrees to about 95 degrees, and more narrowly from about 80 degrees to about 95 degrees. By comparison, the interior angle φ between struts of the base pattern 40 is greater than 100 degrees, and is from about 115 degrees to about 130 degrees. It will be appreciated that the struts 730 of the new pattern 700 of FIG. 9 are oriented closer to the axial direction (horizontal arrow 43) than the struts of the base pattern 40 of FIG. 5, which can cause a change in strength of the individual struts and a change in hoop strength of the rings formed by the struts. As previously indicated, the angles and the orientation of the struts affects mechanical properties due to the radial expansion of the extruded tube during the blow molding process and the resulting molecular orientation of polymer chains. With a large amount of radial expansion during blow molding, molecular polymer chain orientation could be expected to be more circumferential than axial, in which case, structural elements of the stent scaffold which are oriented closer to the axial direction (horizontal arrow 43) could be expected to be less rigid than structural elements oriented closer to the circumferential direction (vertical arrow 41). On the other hand, with a small amount of radial expansion during blow molding, molecular polymer chain orientation could be expected to be more axial than circumferential, in which case, structural elements of the stent scaffold which are oriented closer to the axial direction (horizontal arrow 43) could be expected to be more rigid than structural elements oriented closer to the circumferential direction (vertical arrow 41). Any change in axial elongation during the blow molding process can also affect molecular polymer chain orientation as well as rigidity and flexibility of stent scaffold structural elements.

Referring again to FIG. 9, the struts 730, bending elements 732, and links 734 define the plurality of W-shaped closed cells 736. The W-shapes appear rotated 90 degrees. Each of the W-shaped cells 736 is immediately surrounded by six other W-shaped cells 736, meaning that the perimeter of each W-shaped cell 736 merges with a portion of the perimeter of six other W-shaped cells 736. Stated another way, each W-shaped cell 736 abuts or touches six other W-shaped cells 736. There are exactly three W-shaped closed cells 736 that span the circumferential dimension of the pattern. Also, each pair of adjacent rings 713 forms exactly three W-shaped closed cells.

The perimeter of each W-shaped cell 736 includes eight of the struts 730, two of the links 734, and ten of the bending elements 732. Four of the eight struts form a proximal side of the cell perimeter and the other four struts form a distal side of the cell perimeter. The opposing struts on the proximal and distal sides are substantially parallel to each other.

A stent according to the present invention can comprise a stent scaffold fabricated as described above using a base pattern or a new pattern derived from a base pattern. The stent scaffold can be covered with a drug coating and/or the stent scaffold itself can be impregnated or infused with a drug. The drug elutes from the stent scaffold after deployment.

The drug carried within and/or on the stent scaffold can be any suitable therapeutic agent known in the art of stents and other implantable devices. The therapeutic agent can be in a substantially pure form. The therapeutic agent can be mixed, dispersed, dissolved, encapsulated or otherwise carried in a polymer.

Therapeutic agents include without limitation an anti-restenosis agent, an antiproliferative agent, an anti-inflammatory agent, an antineoplastic, an antimitotic, an antiplatelet, an anticoagulant, an antifibrin, an antithrombin, a cytostatic agent, an antibiotic, an anti-enzymatic agent, an angiogenic agent, a cyto-protective agent, a cardioprotective agent, a proliferative agent, an ABC A1 agonist, an antioxidant, a cholesterol-lowering agent, aspirin, an angiotensin-converting enzyme, a beta blocker, a calcium channel blocker, nitroglycerin, a long-acting nitrate, a glycoprotein IIb-IIIa inhibitor or any combination thereof.

Examples of antiproliferative agents include, without limitation, actinomycins, taxol, docetaxel, paclitaxel, rapamycin, 40-O-(3-hydroxy)propyl-rapamycin, 40-O-[2-(2-hydroxy) ethoxy]ethyl-rapamycin, or 40-O-tetrazole-rapamycin, 40-epi-(N1-tetrazolyl)-rapamycin, ABT-578, zotarolimus, everolimus, biolimus, novolimus, myolimus, deforolimus, temsirolimus, perfenidone and derivatives, analogs, prodrugs, co-drugs and combinations of any of the foregoing.

While several particular forms of the invention have been illustrated and described, it will also be apparent that various modifications can be made without departing from the scope of the invention. For example, it will be appreciated that the method of deriving a new pattern from a base pattern can be performed with a base pattern other than the base pattern of FIG. 5. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A method of manufacturing a stent, the method comprising:
    determining a shape of a first stent scaffold radially compressed to a reduced outer diameter, the stent scaffold capable of being deployed to an expanded outer diameter;
    determining a pattern from the determined shape;
    fabricating a precursor tube by extruding a substrate polymer including poly L-lactic acid (PLLA), the precursor tube having the reduced outer diameter; and
    forming a second stent scaffold by applying the determined pattern to the precursor tube, the second stent scaffold capable of being deployed to the expanded outer diameter.

2. The method of claim 1, wherein determining the shape of the first stent scaffold comprises constructing a numerical model of the first stent scaffold and simulating radial compression of the numerical model to the reduced outer diameter.

3. The method of claim 2, wherein determining the pattern comprises selecting control points on the numerical model, determining new positions of the control points after the simulating of radial compression, and using the new positions to design the pattern.

4. The method of claim 1, wherein determining the shape of the first stent scaffold comprises radially compressing the first stent scaffold.

5. The method of claim 4, wherein determining the pattern comprises identifying control points on the first stent scaffold, determining new positions of the control points after the first stent scaffold is radially compressed, and using the new positions to design the pattern.

6. The method of claim 1, the second stent scaffold is capable of being crimped to an outer diameter less than the reduced outer diameter without damage and capable of being deployed up to an outer diameter greater than the reduced outer diameter.

7. The method of claim 6, wherein the determined pattern includes a plurality of W-shaped closed cells.

8. A method of manufacturing a stent, the method comprising:
    providing a precursor tube made of a substrate polymer including poly L-lactic acid (PLLA);
    forming a stent scaffold by applying a pattern of struts on the precursor tube, the pattern comprising a plurality of serpentine rings that define closed cells, each closed cell bounded by struts that are partly linear, bending elements, and links, wherein the serpentine rings are defined by the partly linear struts and the bending elements, the links connecting each one of the serpentine rings to another one of the serpentine rings, the struts oriented in such a way to form interior angles of between 80 degrees and 95 degrees between every two adjacent struts.

9. The method of claim 8, wherein the precursor tube is fabricated from an extruded tube.

10. The method of claim 9, wherein the precursor tube is fabricated from the extruded tube having been radially expanded to a first outer diameter, the stent scaffold is capable of being crimped to a second outer diameter less than the first outer diameter without damage and capable of being deployed after crimping to a third outer diameter greater than the first outer diameter.

11. A polymeric stent comprising:
    a stent scaffold made of a substrate polymer including poly L-lactic acid (PLLA), the stent scaffold comprising a plurality of struts forming a plurality of rings, each pair of adjacent rings connected to each other by links, there being exactly three closed cells enclosed within each pair of adjacent rings, the struts being oriented in such a way to form interior angles of between 80 degrees and 95 degrees between every two adjacent struts.

12. The polymeric stent of claim 11, wherein the stent scaffold is cut from a precursor tube having an outer diameter of about 3.0 mm, the precursor tube fabricated from an extruded tube made of PLLA, the extruded tube being radially expanded to an outer diameter of about 3.0 mm.

13. The polymeric stent of claim 11, wherein the stent scaffold has an outer diameter of about 3.0 mm.

14. The polymeric stent of claim 13, wherein the stent scaffold is capable of being crimped to an outer diameter of about 1.3 mm without damage and capable of being deployed up to an outer diameter of about 3.8 mm.

15. The polymeric stent of claim 13, wherein the stent scaffold is formed from a pattern of struts derived from another stent scaffold radially compressed to an outer diameter of about 3.0 mm.

16. The polymeric stent of claim 15, wherein the stent scaffold and the other stent scaffold are both capable of being deployed up to an outer diameter of about 3.8 mm.

* * * * *